United States Patent
Nagai et al.

(10) Patent No.: US 10,388,878 B2
(45) Date of Patent: *Aug. 20, 2019

(54) FULLERENE DERIVATIVE AND N-TYPE SEMICONDUCTOR MATERIAL

(71) Applicants: DAIKIN INDUSTRIES, LTD., Osaka (JP); OSAKA UNIVERSITY, Osaka (JP)

(72) Inventors: Takabumi Nagai, Osaka (JP); Kenji Adachi, Osaka (JP); Yoshio Aso, Osaka (JP); Yutaka Ie, Osaka (JP); Makoto Karakawa, Osaka (JP)

(73) Assignees: DAIKIN INDUSTRIES, LTD., Osaka (JP); OSAKA UNIVERSITY, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/891,416

(22) PCT Filed: May 16, 2014

(86) PCT No.: PCT/JP2014/063126
§ 371 (c)(1),
(2) Date: Nov. 16, 2015

(87) PCT Pub. No.: WO2014/185535
PCT Pub. Date: Nov. 20, 2014

(65) Prior Publication Data
US 2016/0126462 A1    May 5, 2016

(30) Foreign Application Priority Data

May 16, 2013  (JP) ................................ 2013-104475
Sep. 2, 2013  (JP) ................................ 2013-181678

(51) Int. Cl.
*H01L 51/00* (2006.01)
*C07D 209/70* (2006.01)
*C08K 3/04* (2006.01)
*H01L 51/42* (2006.01)

(52) U.S. Cl.
CPC ........ *H01L 51/0047* (2013.01); *C07D 209/70* (2013.01); *C08K 3/045* (2017.05); *H01L 51/005* (2013.01); *H01L 51/0036* (2013.01); *H01L 51/0037* (2013.01); *C08G 2261/124* (2013.01); *C08G 2261/3142* (2013.01); *C08G 2261/3223* (2013.01); *C08G 2261/3243* (2013.01); *C08G 2261/91* (2013.01); *H01L 51/4253* (2013.01); *Y02E 10/549* (2013.01)

(58) Field of Classification Search
CPC ............. H01L 51/0047; H01L 51/0036; H01L 51/0037; H01L 51/005; H01L 51/4253; C08K 3/045; C07D 209/70; C08G 2261/124; C08G 2261/3142; C08G 2261/3223; C08G 2261/3243; C08G 2261/91; Y02E 10/549
See application file for complete search history.

(56) References Cited

U.S. PATENT DOCUMENTS

| 2010/0127244 | A1* | 5/2010 | Kronholm | B82Y 10/00 257/40 |
| 2010/0249447 | A1* | 9/2010 | Lada | B01D 15/08 560/129 |
| 2011/0001093 | A1 | 1/2011 | Itoh et al. | |
| 2011/0193073 | A1 | 8/2011 | Itoh et al. | |
| 2014/0182674 | A1 | 7/2014 | Higashi et al. | |

FOREIGN PATENT DOCUMENTS

| EP | 2 998 293 | 3/2016 |
| JP | 9-74216 | 3/1997 |
| JP | 2008-280323 | 11/2008 |

(Continued)

OTHER PUBLICATIONS

Cowan et al. (Adv. Funct. Mater. 2011, 21, 3083-3092).*

(Continued)

*Primary Examiner* — Robert H Havlin
(74) *Attorney, Agent, or Firm* — Wenderoth, Lind & Ponack, L.L.P.

(57) ABSTRACT

The present invention is a material having excellent performance as an n-type semiconductor material, in particular for organic thin-film solar cells.

The present invention provides an n-type semiconductor consisting of a fullerene derivative having a purity of 99% or more, the fullerene derivative being represented by formula (1):

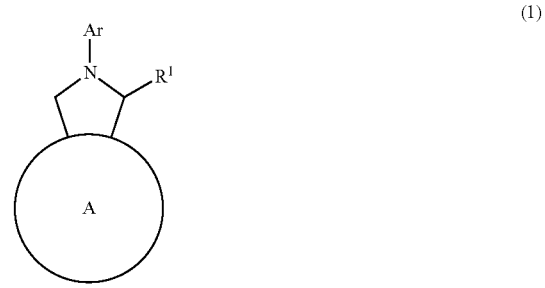

(1)

wherein ring A represents $C_{60}$ fullerene;

R1 represents a hydrogen atom, alkyl optionally having at least one substituent, or aryl optionally having at least one substituent; and Ar represents aryl optionally substituted with at least one alkyl group.

10 Claims, No Drawings

(56) References Cited

FOREIGN PATENT DOCUMENTS

| | | |
|---|---|---|
| JP | 2009-13246 | 1/2009 |
| JP | 2009-84264 | 4/2009 |
| JP | 2009-542725 | 12/2009 |
| JP | 2010-92964 | 4/2010 |
| JP | 2011-502363 | 1/2011 |
| JP | 2011-236109 | 11/2011 |
| JP | 2012-89538 | 5/2012 |
| JP | 2012-94829 | 5/2012 |
| JP | 2012-142407 | 7/2012 |
| JP | 2012-151171 | 8/2012 |
| JP | 2012-162506 | 8/2012 |
| JP | 2012-520826 | 9/2012 |
| JP | 2013-016669 | 1/2013 |
| JP | 2013-23752 | 2/2013 |
| JP | 2013-069663 | 4/2013 |
| WO | 2008/006071 | 1/2008 |
| WO | 2009/058811 | 5/2009 |
| WO | 2010/107924 | 9/2010 |
| WO | 2013/015441 | 1/2013 |

OTHER PUBLICATIONS

Hirsch et al. (Fullerenes: Chemistry and Reactions, 2005, 423 pages, pp. 24-29 provided).*

Doome et al. (J. Phys. Chem Solids, vol. 58, No. II, pp. 1839-1843, 1997).*

Troshin et al. (Russian Chemical Bulletin, International Edition, vol. 57, No. 5, pp. 887-912, May 2008).*

International Search Report dated Aug. 12, 2014 in corresponding International Application No. PCT/JP2014/063126 (with English translation).

Hou et al., "Synthesis, Characterization, and Photovoltaic Properties of a Low Band Gap Polymer Base on Silole-Containing Polythiophenes and 2,1,3-Benzothiadiazole," Journal of American Chemical Society, 2008, vol. 130, No. 48, pp. 16144-16145.

Hammond et al., "Molecular Order in High-Efficiency Polymer/Fullerene Bulk Heterojunction Solar Cells," ACS Nano, 2011, vol. 5, No. 10, pp. 8248-8257.

Matsumoto et al., "Design of fulleropyrrolidine derivatives as an acceptor molecule in a thin layer organic solar cell," Journal of Materials Chemistry, 2010, vol. 20, pp. 9226-9230.

Moriwaki et al., "Synthesis and properties of novel methanofullerenes having ethylthienyl and/or n-pentyl group for photovoltaic cells," Tetrahedron Journal, 2010, vol. 66, pp. 7316-7321.

He et al., "Indene-C60 Bisadduct: A New Acceptor for High-Performance Polymer Solar Cells," Journal of the American Chemical Society, 2010, vol. 132, No. 4, pp. 1377-1382.

Hoke et al., "Recombination in Polymer: Fullerene Solar Cells with Open-Circuit Voltages Approaching and Exceeding 1.0 V," Advanced Energy Materials, 2013, vol. 3, pp. 220-230.

Extended European Search Report dated Dec. 14, 2016 in corresponding European Application No. 14798196.3.

Leo et al., "Interfacial Properties of Substituted Fulleropyrrolidines on the Water Surface", Langmuir, vol. 16, No. 10, 2000, pp. 4599-4606.

Armaroli et al., "Photoinduced processes in fullerenopyrrolidine and fullerenopyrazoline derivatives substituted with an oligophenylenevinylene moiety", Journal of Materials Chemistry, vol. 12, No. 7, 2002, pp. 2077-2087.

Vasapollo et al., "Synthesis of novel nitroso-fulleropyrrolidines", Tetrahedron Letters, vol. 43, No. 28, 2002, pp. 4969-4972.

Attanasi et al., "Synthesis of Fullerene-Cardanol Derivatives", Synlett, 2004, No. 5, 2004, pp. 799-802.

Nakamura et al., "Photoreactions between [60]Fullerene and Various Aromatic Tertiary Amines", The Journal of Organic Chemistry, vol. 70, No. 21, 2005, pp. 8472-8477.

Saha et al., "A Photoactive Molecular Triad as a Nanoscale Power Supply for a Supramolecular Machine", Chemistry—A European Journal, vol. 11, No. 23, 2005, pp. 6846-6858.

Saha et al., "A Redox-Driven Multicomponent Molecular Shuttle", Journal of the American Chemical Society, vol. 129, No. 40, 2007, pp. 12159-12171.

Tong et al., "N-Unsubstituted and N-Arylated Fulleropyrrolidines: New Useful Building Blocks for $C_{60}$ Functionalization", Chinese Journal of Chemistry, vol. 24, No. 9, 2006, pp. 1175-1179.

Kunsági-Máté et al., "Effect of covalent functionalization of $C_\alpha$ fullerene on its encapsulation by water soluble calixarenes" Journal of Inclusion Phenomena and Macrocyclic Chemistry, vol. 60, No. 1-2, 2008, pp. 71-78.

Attanasi et al., "Synthesis and characterization of novel cardanol based fulleropyrrolidines", ARKIVOC, vol. 2009 No. 8, 2008, pp. 69-84.

Fock et al., "A statistical approach to inelastic electron tunneling spectroscopy on fullerene-terminated molecules", Physical Chemistry Chemical Physics, vol. 13, No. 32, 2011, pp. 14325-14332.

Sorensen et al., "Fulleropyrrolidine End-Capped Molecular Wires for Molecular Electronics—Synthesis, Spectroscopic, Electrochemical, and Theoretical Characterization", The Journal of Organic Chemistry, vol. 76, No. 1, 2010, pp. 245-263.

Zhu et al., "Study on the thermal reactions of [60]fullerene with amino acids and amino acid esters", Organic & Biomolecular Chemistry, vol. 10, No. 43, 2012, pp. 8720-8729.

* cited by examiner

FULLERENE DERIVATIVE AND N-TYPE SEMICONDUCTOR MATERIAL

TECHNICAL FIELD

The present invention relates to a fullerene derivative, an n-type semiconductor material, and the like.

BACKGROUND ART

Organic thin-film solar cells are formed by a coating technique with a solution of an organic compound, which is a photoelectric conversion material. The cells have various advantages: for example, 1) device production cost is low; 2) area expansion is easy; 3) the cells are more flexible than inorganic materials, such as silicon, thus enabling a wider range of applications; and 4) resource depletion is less likely. As such, organic thin-film solar cells have been developed, and the use of the bulk heterojunction structure has particularly led to a significant increase in photoelectric conversion efficiency, thus attracting widespread attention.

For p-type semiconductor of the photoelectric conversion basic materials used for organic thin-film solar cells, poly-3-hexylthiophene (P3HT) is particularly known as an organic p-type semiconductor material exhibiting excellent performance. With an aim to obtain advanced materials, recent developments have provided compounds (donor-acceptor type π-conjugated polymers) that can absorb broad wavelengths of solar light or that have tuned energy levels, leading to significant improvements in the performance of materials. Examples of such compounds include poly-p-phenylenevinylene and poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7).

For n-type semiconductors as well, fullerene derivatives have been intensively studied, and [6,6]-phenyl-$C_{61}$-butyric acid methyl ester (PCBM) has been reported as a material having excellent photoelectric conversion performance (see the below-listed Patent Documents 1, 2, etc.). Nonetheless, there have been few reports that demonstrate stable and excellent photoelectric conversion efficiency of fullerene derivatives except for PCBM.

Although fullerene derivatives for organic solar cells other than PCBM have been reported, the reports concern a comparison using special devices from which a power collection material of the positive electrode (ITO electrode) is removed (Non-patent Document 1), or fullerene derivatives only showing performance almost equivalent to that of PCBM (Non-patent Document 2). Moreover, although the disubstituted derivatives reported by Y. Li et al. (Non-patent Document 3), when used with P3TH, achieved higher conversion efficiency than PCBM as reported by E. T. Hoke et al., the disubstituted derivatives exhibited only low conversion efficiency when used with a donor-acceptor type π-conjugated polymer (Non-patent Document 4).

Thus, except for PCBM, advanced n-type materials capable of achieving high conversion efficiency, independently of p-type materials, have been unknown.

Several methods for synthesizing fullerene derivatives have been proposed. Methods known to be excellent from the standpoint of yield and purity include a method for synthesizing, using a diazo compound, a fullerene derivative having a 3-membered ring moiety and a method for synthesizing a fullerene derivative having a 5-membered ring moiety to which an azomethine ylide generated from a glycine derivative and an aldehyde is added.

The aforementioned PCBM is a fullerene derivative having a 3-membered ring moiety, and PCBM can be obtained by preparing a mixture of three types of products each having a fullerene backbone to which a carbene intermediate is added, and subjecting the mixture to a conversion reaction by light irradiation or heat treatment. However, the derivative having a 3-membered ring moiety obtained by this production method is restricted in terms of the introduction site of substituent and the number of substituents; thus, the development of novel n-type semiconductors has significant limitations.

Fullerene derivatives having a 5-membered ring moiety, on the other hand, are considered to be excellent because of their diverse structures. However, there have been few reports on the fullerene derivatives having excellent performance as an n-type semiconductor material for organic thin-film solar cells. One of a few examples is the fullerene derivative disclosed in the below-listed Patent Document 3.

CITATION LIST

Patent Document

Patent Document 1: JP2009-084264A
Patent Document 2: JP2010-092964A
Patent Document 3: JP2012-089538A

Non-Patent Documents

Non-patent Document 1: T. Itoh et al., Journal of Materials Chemistry, 2010, vol. 20, page 9,226
Non-patent Document 2: T. Ohno et al., Tetrahedron, 2010, vol. 66, page 7, 316
Non-patent Document 3: Y. Li et al., Journal of American Chemical Society, 2010, vol. 132, page 1,377
Non-patent Document 4: E. T. Hoke et al., Advanced Energy Materials, 2013, vol. 3, page 220

SUMMARY OF INVENTION

Technical Problem

Patent Document 3 states that the fullerene derivative disclosed therein exhibits high photoelectric conversion efficiency. However, further improvement of photoelectric conversion efficiency has been desired.

Specifically, the main object of the present invention is to provide a material exhibiting excellent performance as an n-type semiconductor, in particular an n-type semiconductor for photoelectric conversion elements such as organic thin-film solar cells.

Solution to Problem

The fullerene derivatives disclosed in the Examples of Patent Document 3 were all considered to have a high purity because the derivatives were purified by preparative GPC. In fact, the results of HPCL analysis conducted by the present inventors also indicated that the derivatives were substantially pure products.

Thus, it appeared that the fullerene derivatives, even if further purified, would not exhibit further improved photoelectric conversion efficiency.

Surprisingly, however, among the fullerene derivatives purified by preparative GPC in the Examples of Patent Document 3, the fullerene derivative represented by the following formula (1), when further purified, achieved a remarkable improvement in photoelectric conversion efficiency,

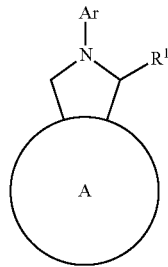

(1)

wherein ring A is $C_{60}$ fullerene;
$R^1$ represents alkyl optionally having at least one substituent, or aryl optionally having at least one substituent; and
Ar represents aryl optionally substituted with at least one alkyl group. While HPCL analysis did not clearly indicate the improvement in purity achieved by this further purification, elemental analysis revealed a certain amount of improvement in the purity.

The present inventors further conducted extensive research based on these findings, and completed the present invention.

The present invention includes the following embodiments, and the like.

Item 1.

An n-type semiconductor material consisting of a fullerene derivative having a purity of 99% or more as defined below, the fullerene derivative being represented by formula (1):

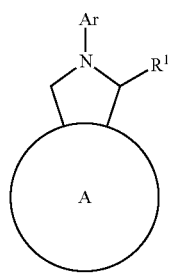

(1)

wherein ring A represents $C_{60}$ fullerene;
$R^1$ represents alkyl optionally having at least one substituent, or aryl optionally having at least one substituent; and
Ar represents aryl optionally substituted with at least one alkyl group,
the purity being defined by the following equation:

Purity (%)=100−$D_{max}$ (%)

wherein $D_{max}$ is the maximum value among the absolute value of the difference between an analysis value and a theoretical value obtained in the elemental analysis of carbon, the absolute value of the difference between an analysis value and a theoretical value obtained in the elemental analysis of hydrogen, and the absolute value of the difference between an analysis value and a theoretical value obtained in the elemental analysis of nitrogen.

Item 2.

The n-type semiconductor material according to Item 1, which is for use in an organic thin-film solar cell.

Item 3.

An organic power-generating layer comprising the n-type semiconductor material according to Item 2 and a p-type semiconductor material.

Item 4.

The organic power-generating layer according to any one of Items 1 to 3, wherein the p-type semiconductor material consists of a donor-acceptor type π-conjugated polymer, the donor-acceptor type π-conjugated polymer having as a donor unit benzodithiophene, dithienosilole, or N-alkyl carbazole, and as an acceptor unit benzothiadiazole, thienothiophene, or thiophene pyrrole dione.

Item 5.

The organic power-generating layer according to Item 4, wherein the donor-acceptor type π-conjugated polymer is poly(thieno[3,4-b]thiophene-co-benzo[1,2-b:4,5-b']thiophene), or poly(dithieno[1,2-b:4,5-b'][3,2-b:2',3'-d]silole-alt-(2,1,3-benzothiadiazole).

Item 6.

The organic power-generating layer according to Item 4, wherein the donor-acceptor type π-conjugated polymer is poly(thieno[3,4-b]thiophene-co-benzo[1,2-b:4,5-b']thiophene).

Item 7.

The organic power-generating layer according to any one of Items 1 to 6, wherein the p-type semiconductor material is poly-3-hexylthiophene, or poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]].

Item 8.

The organic power-generating layer according to any one of Items 1 to 7, further comprising diiodooctane.

Item 9.

A photoelectric conversion element comprising the organic power-generating layer according to any one of Items 3 to 8.

Item 10.

The photoelectric conversion element according to Item 9, which is an organic thin-film solar cell.

Item 11.

The n-type semiconductor material according to Item 1, which is for use in a photosensor array.

Item 12.

The photoelectric conversion element according to Item 9, which is a photosensor array.

Item 1A.

An n-type semiconductor material consisting of a fullerene derivative having a purity of 99% or more as defined below, the fullerene derivative being represented by formula (1A):

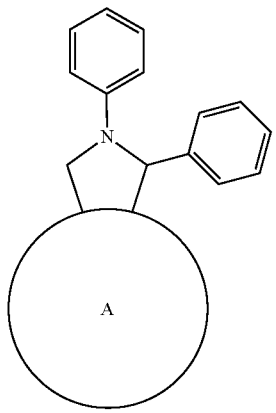

(1A)

wherein ring A represents $C_{60}$ fullerene,
the purity being defined by the following equation:

Purity (%) = 100 − $D_{max}$ (%)

wherein $D_{max}$ is the maximum value among the absolute value of the difference between an analysis value and a theoretical value obtained in the elemental analysis of carbon, the absolute value of the difference between an analysis value and a theoretical value obtained in the elemental analysis of hydrogen, and the absolute value of the difference between an analysis value and a theoretical value obtained in the elemental analysis of nitrogen.

Item 2A.

The n-type semiconductor material according to Item 1A, which is for use in an organic thin-film solar cell.

Item 3A.

An organic power-generating layer comprising the n-type semiconductor material according to Item 2A and a p-type semiconductor material.

Item 4A.

The organic power-generating layer according to any one of Items 1A to 3A, wherein the p-type semiconductor material consists of a donor-acceptor type π-conjugated polymer, the donor-acceptor type π-conjugated polymer including as a donor unit benzodithiophene, dithienosilole, or N-alkyl carbazole and as an acceptor unit benzothiadiazole, thienothiophene, or thiophene pyrrole dione.

Item 5A.

The organic power-generating layer according to Item 4A, wherein the donor-acceptor type π-conjugated polymer is poly(thieno[3,4-b]thiophene-co-benzo[1,2-b:4,5-b']thiophene), or poly(dithieno[1,2-b:4,5-b'][3,2-b:2',3'-d]silole-alt-(2,1,3-benzothiadiazole).

Item 6A.

The organic power-generating layer according to Item 4A, wherein the donor-acceptor type π-conjugated polymer is poly(thieno[3,4-b]thiophene-co-benzo[1,2-b:4,5-b']thiophene).

Item 7A.

The organic power-generating layer according to any one of Items 1A to 6A, wherein the p-type semiconductor material is poly-3-hexylthiophene, or poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]].

Item 8A.

The organic power-generating layer according to any one of Items 1A to 7A, further comprising diiodooctane.

Item 9A.

A photoelectric conversion element comprising the organic power-generating layer according to any one of Items 3A to 8A.

Item 10A.

The photoelectric conversion element according to Item 9A, which is an organic thin-film solar cell.

Item 11A.

The n-type semiconductor material according to Item 1A, which is for use in a photosensor array.

Item 12A.

The photoelectric conversion element according to Item 9A, which is a photosensor array.

Advantageous Effects of Invention

The n-type semiconductor material according to the present invention is useful, particularly as an n-type semiconductor for photoelectric conversion elements such as organic thin-film solar cells, and the material can achieve high photoelectric conversion efficiency.

DESCRIPTION OF EMBODIMENTS

The following describes the n-type semiconductor material, and the like according to the present invention in detail.

n-Type Semiconductor Material

The n-type semiconductor material according to the present invention consists of a fullerene derivative having a purity of 99% or more as defined below, the fullerene derivative being represented by formula (1):

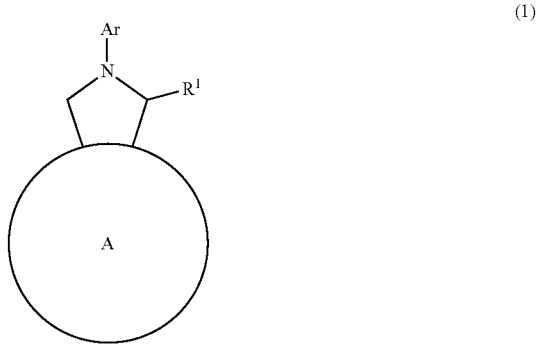

(1)

wherein ring A represents $C_{60}$ fullerene;
$R^1$ represents alkyl optionally having at least one substituent, or aryl optionally having at least one substituent; and
Ar represents aryl optionally substituted with at least one alkyl group.

Thus, the n-type semiconductor material according to the present invention can be an n-type semiconductor material consisting of the fullerene derivative represented by formula (1) having a purity of 99% or more as defined above.

As used herein, "alkyl" refers to $C_{1-8}$ alkyl (preferably $C_{1-6}$ alkyl) such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

As used herein, "aryl" refers to $C_{6-14}$ aryl, such as phenyl, 1-naphthyl, 2-naphthyl, 2-biphenylyl, 3-biphenylyl, 4-biphenylyl, and 2-anthryl.

Examples of substituents in "alkyl optionally having at least one substituent" represented by $R^1$ include alkoxy, alkoxycarbonyl, and polyether.

The number of the substituents is preferably 1.

As used herein, examples of alkoxy include groups represented by formula $R^a$—O— wherein $R^a$ represents alkyl.

As used herein, examples of alkoxycarbonyl include groups represented by formula $R^a$—O—CO— wherein $R^a$ represents alkyl.

As used herein, examples of polyether include groups represented by formula $R^a$—$(OR^b)_n$—O— wherein $R^a$ and $R^b$ are the same or different, and each represents alkyl, $R^b$ may be the same or different in each occurrence, and n represents an integer of 1 to 4.

Examples of substituents in "aryl optionally having at least one substituent" represented by $R^1$ include halogen atoms.

As used herein, examples of halogen atoms include fluorine, chlorine, bromine, and iodine.

The number of substituents is preferably 0 (no substitution) to 2.

The "aryl optionally having at least one substituent" represented by $R^1$ is preferably phenyl optionally substituted with one or two fluorine atoms.

Ar is preferably phenyl optionally substituted with one alkyl group, and more preferably phenyl.

The fullerene derivative represented by formula (1) is preferably, for example, represented by formula (1A):

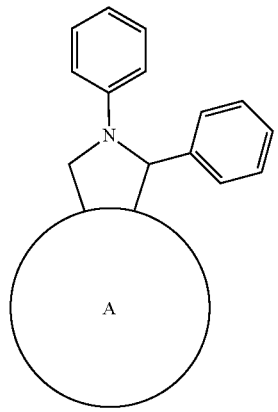

(1A)

wherein ring A represents $C_{60}$ fullerene,
a fullerene derivative represented by formula (1B):

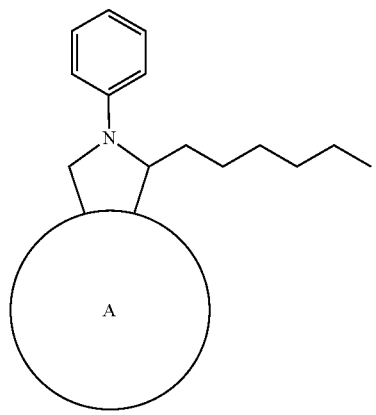

(1B)

wherein ring A represents $C_{60}$ fullerene, or
a fullerene derivative represented by formula (1C):

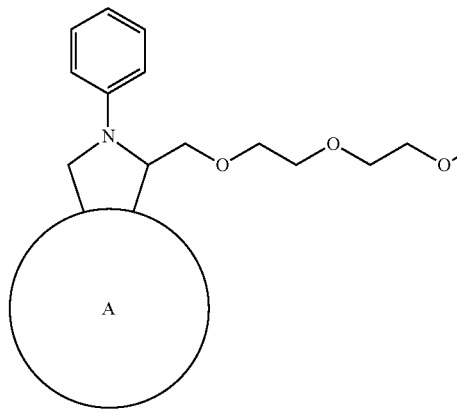

(1C)

wherein ring A represents $C_{60}$ fullerene.

The purity is preferably 99.0% or more, more preferably 99.1% or more, further more preferably 99.2% or more, still more preferably 99.3% or more, and yet more preferably, 99.4% or more, 99.5% or more, 99.6% or more, or 99.7% or more.

The purity is defined by the following equation:

Purity (%)=100–$D_{max}$ (%)

wherein $D_{max}$ is the maximum value among the absolute value of the difference between an analysis value and a theoretical value obtained in the elemental analysis of carbon, the absolute value of the difference between an analysis value and a theoretical value obtained in the elemental analysis of hydrogen, and the absolute value of the difference between an analysis value and a theoretical value obtained in the elemental analysis of nitrogen.

The symbol "%" used in the elemental analysis denotes percent by mass.

Specifically, when the absolute value of the difference between an analysis value and a theoretical value obtained in the elemental analysis of carbon, hydrogen, and nitrogen is indicated as $D_{carbon}$, $D_{hydrogen}$, and $D_{nitrogen}$, for example, with the value of $D_{carbon}$ being the maximum among them, $D_{max}$ is $D_{carbon}$. In this case, the purity (%) is determined by the following equation.

Purity (%)=100–$D_{carbon}$ (%)

In the specification, the $C_{60}$ fullerene represented by ring A is sometimes indicated by the following structural formula, as often shown in this technical field.

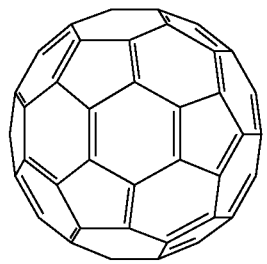 [SMILES: c1c2c3c4c(cc5c6c4c4c7c3c3c1Cc1cc8cc9cc%10cc(c%11c%10c%10c9c9c8c1c3c7c9c%10c4c%116)C5)C2]

$C_{60}$ fullerene is also sometimes described simply as C60.

Specifically, the fullerene derivative represented by formula (1) can be represented, for example, by the following formula (1').

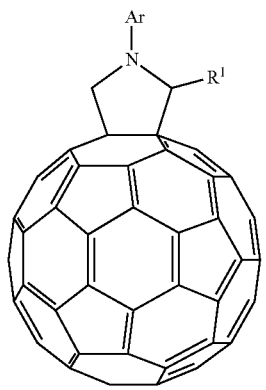

(1')

Because the fullerene derivative represented by formula (1) shows excellent solubility in various organic solvents, it is easy to form a thin film containing the derivative, using a coating technique.

In addition, the fullerene derivative represented by formula (1) easily forms a bulk heterojunction structure, when used as an n-type semiconductor material to prepare an organic power-generating layer, together with an organic p-type semiconductor material.

Method for Producing Fullerene Derivative (1)

The fullerene derivative represented by formula (1) can be synthesized, for example, by a synthesis method disclosed in Patent Document 3, or a method complying therewith.

Specifically, the fullerene derivative represented by formula (1) can be synthesized, for example, in accordance with the following scheme.

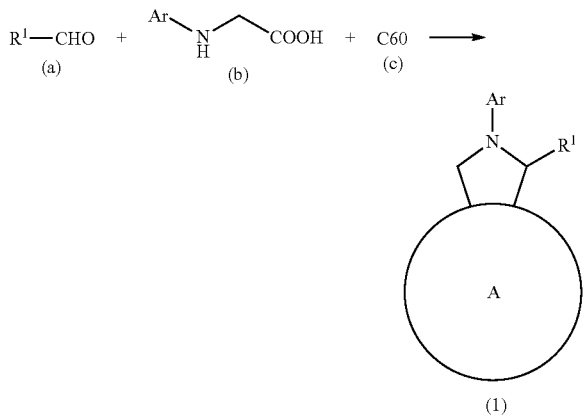

As used herein, Ph in a chemical formula represents phenyl.

Step A

In step A, an N-substituted glycine (compound (b)) is reacted with an aldehyde (compound (a)) and $C_{60}$ fullerene (compound (c)) to thereby obtain a fullerene derivative (compound (1)) represented by formula (1).

Although the amount ratio of the aldehyde (compound (a)), the N-substituted glycine (compound (b)), and the $C_{60}$ fullerene (compound (c)) is arbitrarily determined, the aldehyde compound (compound (a)) and the N-substituted glycine (compound (b)) are each typically added in an amount of 0.1 to 10 moles, and preferably 0.5 to 2 moles, per mole of the $C_{60}$ fullerene (compound (c)), from the standpoint of achieving a high yield.

The reaction is carried out without a solvent or in a solvent.

Examples of solvents include carbon disulfide, chloroform, dichloroethane, toluene, xylene, chlorobenzene, and dichlorobenzene. These solvents may be mixed in suitable proportions for use. Preferable examples of solvents include chloroform, toluene, chlorobenzene, o-dichlorobenzene, and bromobenzene, and particularly preferable examples of solvents include toluene and chlorobenzene.

The reaction temperature is typically within the range of room temperature to about 150° C., and preferably within the range of about 80 to about 120° C. As used herein, the room temperature is within the range of 15 to 30° C.

The reaction time is typically within the range of about 1 hour to about 4 days, and preferably within the range of about 10 to about 24 hours.

The reaction is preferably carried out under reflux with stirring.

The aldehyde (compound (a)), the N-substituted glycine (compound (b)), and the $C_{60}$ fullerene (compound (c)) used in step A are all known compounds, and can be synthesized by a known method (e.g., the method disclosed in Patent Document 3), or a method complying therewith, and also commercially available.

The compound (1) obtained in step A is purified until the purity defined above reaches 99% or more (preferably 99.0% or more, more preferably 99.1% or more, further more preferably 99.2% or more, still more preferably 99.3% or more, and yet more preferably, 99.4% or more).

The purification can be carried out by a conventional purification technique.

Specifically, the purification can be carried out, for example, by the following techniques.

For example, the obtained compound (1) can be purified by silica gel column chromatography (as a developing solvent, for example, hexane-chloroform, hexane-toluene, or hexane-carbon disulfide is preferable), and further purified by HPLC (preparative GPC) (as a developing solvent, for example, chloroform or toluene is preferable, and chloroform is particularly more preferable).

The purified compound (1) is further purified by solvent washing and recrystallization.

In the solvent washing, the solid of the purified compound (1) is preferably washed twice or more with different solvents. The washing may be carried out, for example, by placing the solid of the purified compound (1) in an eggplant flask or the like, and washing the solid using a conventional technique. The washing, when conducted twice or more, preferably includes washing with a solvent having a relatively higher polarity (e.g., methanol and acetone) and washing with a solvent having a relatively lower polarity (e.g., tetrahydrofuran (THF) and hexane). The solvent washing is first preferably carried out with a solvent having a relatively higher polarity in order to reduce the residual solvent. Specifically, the solvent washing is carried out particularly more preferably with methanol, acetone, dichloromethane, tetrahydrofuran (THF), and hexane in this order.

The recrystallization is preferably carried out with, for example, hexane-chlorobenzene, or hexane-carbon disulfide.

It is also effective to purify the compound (1) by an HPLC column intended for fullerene separation, in combination with the solvent washing and the recrystallization purification techniques, or as an alternative technique. The HPLC column for fullerene separation is commercially available, and examples include Cosmosil Buckyprep (Nacalai Tesque, Inc.). The column purification may be carried out twice or more as necessary.

The solvent used in purification by an HPLC column for exclusive use in fullerene separation is at least one member selected from the group consisting of toluene, chloroform, and the like.

From the compound (1) further purified as described above, the solvent is removed. The solvent is preferably removed as follows: first, the supernatant solvent is removed, and the residual solvent left with the solid of the compound (1) is removed by evaporation, followed by drying by heating (e.g., 60 to 100° C., 8 to 24-hour drying) under reduced pressure (e.g., 10 mmHg or less, more preferably 1 mmHg or less).

Use of n-Type Semiconductor Material

The n-type semiconductor material according to the present invention can suitably be used particularly as an n-type semiconductor material for photoelectric conversion elements, such as organic thin-film solar cells and the like.

The n-type semiconductor material according to the present invention is typically used in combination with an organic p-type semiconductor material (organic p-type semiconductor compound).

Examples of organic p-type semiconductor materials include poly-3-hexylthiophene (P3HT), poly-p-phenylenevinylene, poly-alkoxy-p-phenylenevinylene, poly-9,9-dialkylfluorene, and poly-p-phenylenevinylene.

Because of the many approaches to use these materials in solar cells in the past and their ready availability, these materials can easily provide devices that exhibit stable performance.

To achieve higher conversion efficiency, donor-acceptor type π-conjugated polymers capable of absorbing long-wavelength light because of their narrowed bandgap (low bandgap) are effective.

These donor-acceptor type π-conjugated polymers comprise donor units and acceptor units, which are alternately positioned.

Examples of usable donor units include benzodithiophene, dithienosilole, and N-alkyl carbazole, and examples of usable acceptor units include benzothiadiazole, thienothiophene, and thiophene pyrrole dione.

Specific examples include high-molecular compounds obtained by combining these units, such as poly(thieno[3,4-b]thiophene-co-benzo[1,2-b:4,5-b']thiophene) (PTBx series), and poly(dithieno[1,2-b:4,5-b'][3,2-b:2',3'-d]silole-alt-(2,1,3-benzothiadiazole).

Of these, the following are preferable:
(1) poly({4,8-bis[(2-ethylhexyl)oxy]benzo[1,2-b:4,5-b']dithiophene-2,6-diyl}{3-fluoro-2-[(2-ethylhexyl)carbonyl]thieno[3,4-b]thiophenediyl}) (PTB7, the structural formula is shown below);
(2) poly[(4,8-di(2-ethylhexyloxy)benzo[1,2-b:4,5-b']dithiophene)-2,6-diyl-alt-((5-octylthieno[3,4-c]pyrrol-4,6-dione)-1,3-diyl) (PBDTTPD, the structural formula is shown below);
(3) poly[(4,4'-bis(2-ethylhexyl)dithieno[3,2-b:2',3'-d]silole)-2,6-diyl-alt-(2,1,3-benzothiadiazole)-4,7-diyl](PSBTBT, the structural formula is shown below);
(4) poly[N-9''-heptadecanyl-2,7-carbazole-alt-5,5-(4',7'-di-2-thienyl-2',1',3'-benzothiadiazole)](PCDTBT, the structural formula is shown below); and
(5) poly[1-(6-{4,8-bis[(2-ethylhexyl)oxy]-6-methylbenzo[1,2-b:4,5-b']dithiophene-2-yl}{3-fluoro-4-methylthieno[3,4-b]thiophene-2-yl}-1-octanone) (PBDTTT-CF, the structural formula is shown below)

Of these, more preferable examples include PTB-based compounds comprising as an acceptor unit thieno[3,4-b]thiophene having a fluorine atom at position 3, and yet more preferable examples include PBDTTT-CF and PTB7.

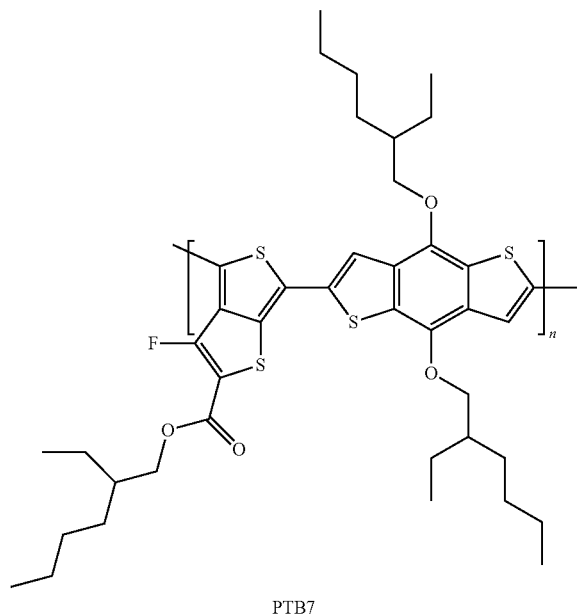

PTB7 wherein n represents the number of repeating units.

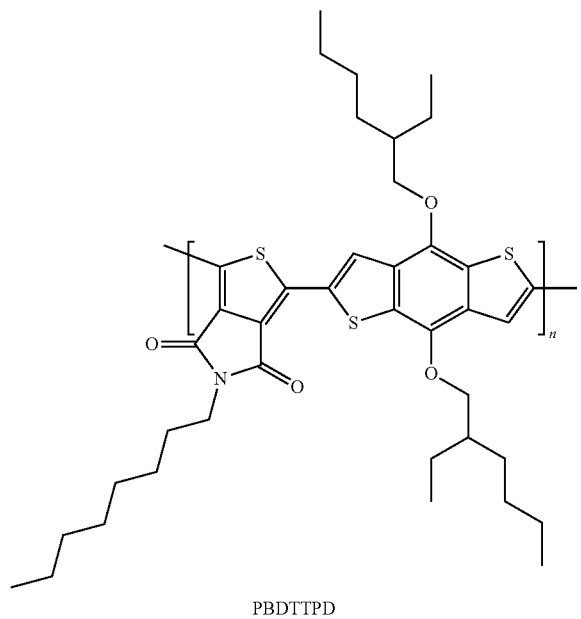

PBDTTPD wherein n represents the number of repeating units.

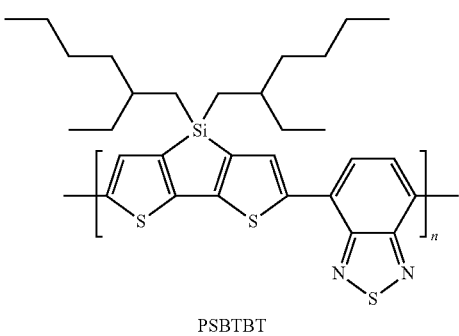

PSBTBT wherein n represents the number of repeating units.

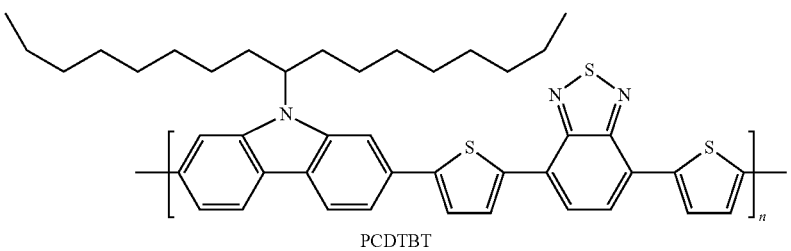

PCDTBT wherein n represents the number of repeating units.

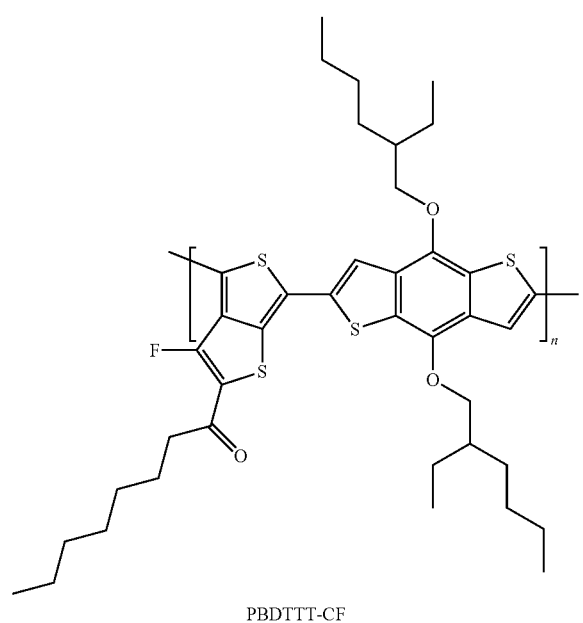

PBDTTT-CF wherein n represents the number of repeating units.

An organic power-generating layer prepared by using the n-type semiconductor material according to the present invention in combination with an organic p-type semiconductor material (preferably, for example, P3HT, or a donor-acceptor type π-conjugated polymeric material, and more preferably, for example, PTB series, such as PTB7) can achieve higher conversion efficiency than an organic power-generating layer prepared by using a conventional n-type semiconductor material consisting of a fullerene derivative such as PCBM.

Because of its excellent solubility in various organic solvents, the n-type semiconductor material according to the present invention enables the preparation of an organic power-generating layer using a coating technique, and also enables easy preparation of an organic power-generating layer having a large area.

The n-type semiconductor material according to the present invention has excellent compatibility with organic p-type semiconductor materials and has a proper self-aggregating property. Thus, the fullerene derivative, when used as an n-type semiconductor material (organic n-type semiconductor material), can easily form an organic power-generating layer having a bulk junction structure. The use of such an organic power-generating layer enables the production of an organic thin-film solar cell or photosensor with high conversion efficiency.

The n-type semiconductor material of the present invention is preferably used alone as an n-type semiconductor material but can also be used in combination with one or more other n-type semiconductor materials. Specifically, the n-type semiconductor material of the present invention may be mixed with one or more other n-type semiconductor materials. Needless to say, the scope of the present invention encompasses such a combination and the use of such a mixture.

Accordingly, the use of the n-type semiconductor material according to the present invention enables the production of an organic thin-film solar cell having excellent performance at low cost.

An alternative application of the organic power-generating layer comprising (or consisting of) the n-type semiconductor material of the present invention is the use of the layer in an image sensor for digital cameras. In response to the demand for advanced functions (higher definition) in digital cameras, existing image sensors consisting of a silicon semiconductor are considered to suffer from lower sensitivity. Amid the demand, recent years have seen promises of achieving higher sensitivity and higher definition by using an image sensor consisting of an organic material with high photosensitivity. Materials for forming the light-receiving part of such a sensor need to absorb light with a high sensitivity and efficiently generate an electrical signal therefrom. In response to this demand, because of its ability to efficiently convert visible light into electrical energy, an organic power-generating layer comprising (or consisting of) the n-type semiconductor material of the present invention can have high performance as a material for the above-described light-receiving part of the sensor.

Organic Power-Generating Layer

The organic power-generating layer according to the present invention comprises the n-type semiconductor material of the present invention and a p-type semiconductor material.

The organic power-generating layer according to the present invention preferably consists of the n-type semiconductor material of the present invention and a p-type semiconductor material.

The organic power-generating layer according to the present invention can be a light converting layer (photoelectric converting layer).

The organic power-generating layer according to the present invention preferably has a bulk heterojunction structure formed by the n-type semiconductor material of the present invention and the above-described organic p-type semiconductor material.

In formation of thin-film formation of an organic power-generating layer, the fullerene derivative according to the present invention has excellent compatibility with organic p-type semiconductor materials (preferably, P3HT, or a donor-acceptor type π-conjugated polymeric material) and suitable self-aggregating property. Therefore, it enables easy production of an organic power-generating layer comprising the n-type semiconductor material of the present invention and an organic p-type semiconductor material, with the layer formed in a bulk heterojunction structure.

The organic power-generating layer according to the present invention further comprises diiodooctane or octanedithiol. This enables the organic power-generating layer of the present invention to achieve high photoelectric conversion efficiency. Although the high photoelectric conversion efficiency, as described later, appears to be attributed to the bulk heterojunction structure formed by the n-type semiconductor material and the organic p-type semiconductor material, the present invention is not limited to this.

The organic power-generating layer according to the present invention is prepared, for example, by dissolving the n-type semiconductor material of the present invention and the aforementioned organic p-type semiconductor material in an organic solvent (an additive can optionally be added), and forming a thin film of the obtained solution on a substrate using a known thin-film forming technique such as spin coating, casting, dipping, inkjet, and screen printing.

The major component of the organic solvent (i.e., a component as a solvent except for additives described later) is, for example, one, or two or more members selected from the group consisting of chloroform, toluene, and chlorobenzene.

The organic solvent preferably contains, as an additive, diiodooctane or octanedithiol. This enables the formation of an organic power-generating layer capable of achieving higher photoelectric conversion efficiency. This appears to be attributed to the bulk heterojunction structure formed by the n-type semiconductor material of the present invention and the aforementioned organic p-type semiconductor material. The diiodooctane content or the octanedithiol content in the organic solvent is typically 1 to 5% (v/v), preferably 2 to 4% (v/v), and particularly preferably 3% (v/v).

To form an effective bulk heterojunction structure for an organic power-generating layer consisting of an n-type semiconductor and a p-type semiconductor, annealing may be conducted after an organic thin film is formed. In particular, when using, as a p-type semiconductor material, P3HT, poly-p-phenylenevinylene, poly-alkoxy-p-phenylenevinylene, poly-9,9-dialkylfluorene, poly-p-phenylenevinylene, or the like, annealing, for example, at 80 to 130° C. for about 10 to 30 minutes can improve conversion efficiency.

However, when using a donor-acceptor type π-conjugated polymer such as PTB7 as a p-type semiconductor material, annealing is unnecessary.

Organic Thin-Film Solar Cell

The organic thin-film solar cell according to the present invention comprises the above-described organic power-generating layer of the present invention.

Thus, the organic thin-film solar cell of the present invention exhibits high photoelectric conversion efficiency.

The structure of the organic thin-film solar cell is not particularly limited, and the organic thin-film solar cell may have the same structure as that of a known organic thin-film solar cell. The organic thin-film solar cell according to the present invention can also be produced in accordance with a known method for producing an organic thin-film solar cell.

One example of the organic thin-film solar cell comprising the fullerene derivative is a solar cell comprising, disposed on a substrate in series, a transparent electrode (positive electrode), a charge transport layer on the positive electrode side, an organic power-generating layer, a charge transport layer on the negative electrode side, and an opposite electrode (negative electrode). The organic power-generating layer is preferably a thin-film semiconductor layer (i.e., a photoelectric conversion layer) comprising an organic p-type semiconductor material and the fullerene derivative of the present invention as an n-type semiconductor material, with the layer formed in a bulk heterojunction structure.

In solar cells having the above-described structure, known materials can suitably be used as materials for layers other than the organic power-generating layer. Specific examples of electrode materials include aluminium, gold, silver, copper, and indium tin oxide (ITO). Examples of charge transport layer materials include PEDOT:PSS (poly(3,4-ethylene dioxythiophene):poly(4-styrenesulfonate)).

Photosensor

As described above, the photoelectric conversion layer obtained by the present invention can effectively function as an image sensor light-receiving part of advanced digital cameras. As compared with conventional photosensors including a silicon photodiode, a photosensor including the photoelectric conversion layer obtained by the present invention can provide an image in a well-lighted area without overexposure as well as a clear image in a poorly lighted area. This makes it possible to obtain an image with higher quality than those of conventional cameras. An photosensor comprises a silicon substrate, an electrode, a light-receiving part consisting of a photoelectric conversion layer, a color filter, and a microlens. The light-receiving part can be about several hundred nanometers in thickness, a fraction of the thickness of conventional silicon photodiodes.

EXAMPLES

The following Examples describe the present invention in more detail. However, the present invention is not limited to the Examples.

The annotation of the symbols and abbreviations used in the Examples is shown below. In addition, symbols and abbreviations typically used in the technical field to which the present invention pertains may also be used throughout this specification.

s: singlet
bs: broad singlet
d: doublet
d-d: double doublet
t: triplet
m: multiplet

Production Example 1: Compound 1

A fullerene derivative (compound 1) was synthesized in accordance with the following reaction formula.

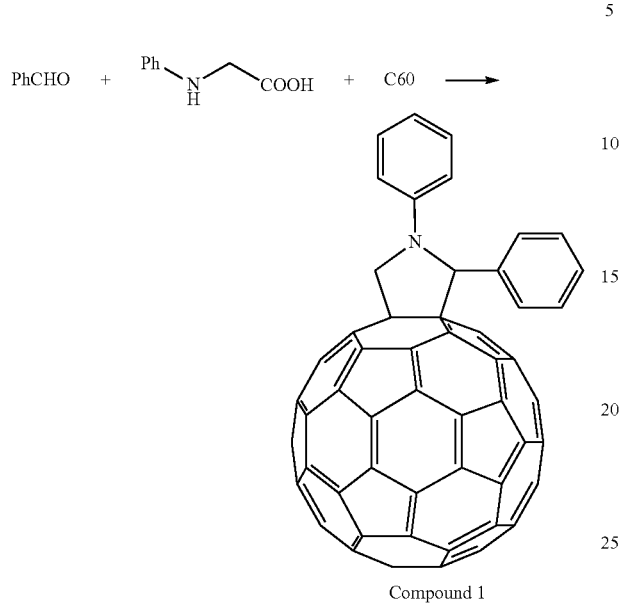

Compound 1

$C_{60}$ fullerene (175 mg, 0.25 mmol), benzaldehyde (27 mg, 0.25 mmol) and N-phenyl glycine (76 mg, 0.5 mmol) were stirred in toluene (100 mL) under reflux for 24 hours. After cooling, the solvent was distilled off, and the product was separated by silica gel column chromatography (n-hexane: toluene=20:1 to 10:1), and further purified by preparative GPC (chloroform), thereby giving sample 1-1 of compound 1. The yield was 29.7%.

The structure of the obtained compound was identified by nuclear magnetic resonance spectrum (NMR): JEOL JNM-ECS400 (400 MHz), and mass spectrum (MS): JEOL JMS-700 (FAB: matrix NBA).

$^1$H-NMR (CDCl$_3$): δ5.00 (1H, d, J=10.5 Hz), 5.68 (1H, d, J=10.5 Hz), 6.08 (1H, s), 7.02-7.10 (1H, m), 7.22-7.40 (7H, m), 7.70-7.81 (2H, m).

MS (FAB+): m/z 916 (M+H). HRMS calcd for C74H13N, 915.1048; found 915.1039.

Sample 1-1 was washed and recrystallized using organic solvents as described below, thereby giving sample 1-2 having higher purity.

Sample 1-1 was placed in an eggplant flask, and washed with methanol, acetone, dichloromethane, THF, and hexane in this order, and further recrystallized with hexane-chlorobenzene.

After removal of the supernatant solvent, the solvent remaining with the obtained solid was evaporated, and further dried under reduced pressure (1 mmHg) using a vacuum pump in a thermostatic bath at 80° C. for 15 hours, thereby giving sample 1-2.

Production Example 2: Compound 2

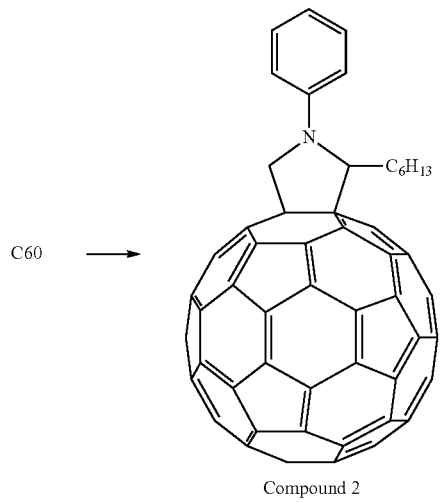

Compound 2

Heptanal (28.5 mg, 0.25 mmol), N-phenylglycine (76 mg, 0.5 mmol), and $C_{60}$ fullerene (175 mg, 0.25 mmol) were stirred in 100 mL of toluene at 110° C. for 24 hours. After cooling, the solvent was distilled off, and the reaction product was separated by column chromatography (SiO$_2$, n-hexane:toluene=10:1) to obtain compound 2 (163 mg, 70.6%). Compound 2 was further purified by preparative GPC (chloroform), thereby giving sample 2-1 of compound 2.

$^1$H-NMR (CDCl3) δ: 0.88 (3H, t, J=6.9 Hz), 1.25-1.40 (4H, m), 1.40-1.60 (2H, m), 1.72-1.86 (2H, m), 2.40-2.52 (1H, m), 2.58-2.70 (1H, m), 5.09 (1H, d, J=10.5 Hz), 5.39 (1H, d, J=10.5 Hz), 5.66 (1H, d-d, J=7.8, 5.0 Hz), 7.00 (1H, d-d, J=7.3, 7.3 Hz), 7.30 (2H, d, J=7.3 Hz), 7.45 (2H, d-d, J=7.3, 7.3 Hz)

Sample 2-1 was further purified by HPLC (column used: Cosmosil Buckyprep, 20ø×250 mm, Nacalai Tesque, Inc., solvent: toluene). The obtained sample was then washed and recrystallized using organic solvents as described below, thereby giving sample 2-2 having higher purity.

Sample 2-1 was placed in an eggplant flask, and washed with methanol, acetone, dichloromethane, THF, and hexane in this order, and further recrystallized with hexane-chlorobenzene.

After removal of the supernatant solvent, the solvent remaining with the obtained solid was evaporated, and further dried under reduced pressure (1 mmHg) using a vacuum pump in a thermostatic bath at 80° C. for 15 hours, thereby giving sample 2-2.

Production Example 3: Compound 3

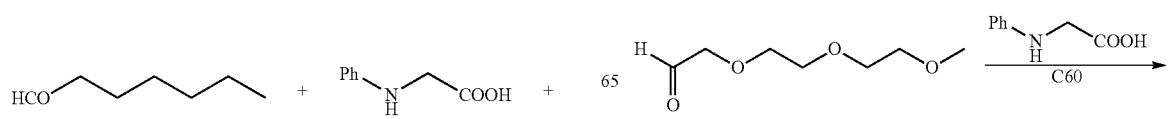

-continued

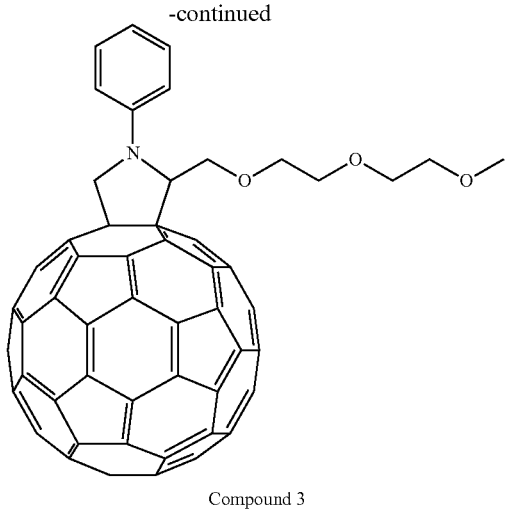

Compound 3

(1) Synthesis Step of 2,5,8-Trioxadecanal 2,5,8-Trioxadecanal was synthesized in accordance with the procedure disclosed in the Journal of Organic Chemistry (1996, vol. 61, page 9,070) as described below.

First, a solution of dimethyl sulfoxide (DMSO) (5 mL) in ethylene chloride (15 mL) was added dropwise to a solution of oxalyl chloride (3 mL) in ethylene chloride (75 mL) at −78° C. 2,5,8-Trioxadecanol (5 mL) and an ethylene chloride solution (30 mL) were added thereto at −78° C., and triethylamine (20 mL) was further added thereto at this temperature, followed by stirring for 30 minutes. The mixture was then further stirred at room temperature for 15 hours. The solvent was distilled off, and the reaction product was separated by silica gel column chromatography (eluent: $CH_2Cl_2$:EtOH=10:1), thereby giving 2,5,8-trioxadecanal.

$^1$H-NMR ($CDCl_3$): δ 3.34 (3H, s), 3.45-3.75 (8H, m), 4.16 (2H, bs), 9.80 (1H, s)

(2) Synthesis Step of Compound 3

N-phenylglycine (76 mg, 0.5 mmol), $C_{60}$ fullerene (360 mg, 0.5 mmol), and 2,5,8-trioxadecanal (324 mg, 0.5 mmol) synthesized in the above procedure were stirred in chlorobenzene (200 mL) at 120° C. for 72 hours. After cooling, the solvent was distilled off, and the product was separated by silica gel column chromatography (toluene:ethyl acetate=50:1) to obtain 194 mg of compound 3 (yield: 40.0%). Compound 3 was further purified by preparative GPC (chloroform), thereby giving sample 3-1 of compound 3.

$^1$H-NMR ($CDCl_3$): δ 3.34 (3H, s), 3.45-3.76 (8H, m), 4.40 (1H, d-d, J=10.3, 2.8 Hz), 4.59 (1H, d-d, J=10.3, 6.2 Hz), 5.30 (2H, s), 5.84 (1H, d, J=6.2, 2.8 Hz), 7.01 (1H, t, J=7.7 Hz), 7.28 (2H, d, J=8.0 Hz), 7.47 (2H, d-d, J=8.0, 7.7 Hz)

Sample 3-1 was further purified by HPLC (column used: Cosmosil Buckyprep, 20⌀×250 mm, Nacalai Tesque, Inc., solvent: toluene). The obtained sample was then washed and recrystallized using organic solvents as described below, thereby giving sample 3-2 having higher purity.

Sample 3-1 was placed in an eggplant flask, and washed with methanol, acetone, dichloromethane, THF, and hexane in this order, and further recrystallized with hexane-chlorobenzene.

After removal of the supernatant solvent, the solvent remaining with the obtained solid was evaporated, and further dried under reduced pressure (1 mmHg) using a vacuum pump in a thermostatic bath at 80° C. for 15 hours, thereby giving sample 3-2.

Determination of Purity of Sample of Compound 1

The purity of each sample 1-1 (Comparative Example 1-1) and sample 1-2 (Example 1-2) of compound 1 was determined by elemental analysis.

The elemental analysis was conducted using a CHN-Corder MT-6 elemental analyzer (Yanaco) as follows: the gasses ($CO_2$, $H_2O$, and $N_2$) obtained by burning each sample were measured to determine the amount ratio, and the mass percent of carbon, hydrogen, and nitrogen was determined based on the amount ratio.

Molecular Formula of Compound 1: $C_{74}H_{13}N$

Theoretical Value of Mass Percent of Carbon, Hydrogen, and Nitrogen (determined by calculating the weight ratio of the carbon, hydrogen, and nitrogen of the compound in consideration of the isotope ratio)

C: 97.04%; H: 1.43%; N: 1.53%

Actual Measured Value of Mass Percent of Carbon, Hydrogen, and Nitrogen

C: 93.78%; H: 1.82%; N: 1.44%

The purity of each sample was determined from the following equation using the maximum absolute value among the differences between the theoretical values and actual measured values of carbon, hydrogen, and nitrogen obtained by elemental analysis.

Purity of Sample (%)=100−$D_{max}$

The following shows the results.

Sample 1-1

Difference between the theoretical value and the actual measured value obtained in the elemental analysis of carbon=−3.26%, $D_{carbon}$=3.26%

Difference between the theoretical value and the actual measured value obtained in the elemental analysis of hydrogen=+0.39%, $D_{hydrogen}$=0.39%

Difference between the theoretical value and the actual measured value obtained in the elemental analysis of nitrogen=−0.09%, $D_{nitrogen}$=0.09%

$D_{max}=D_{carbon}=3.26\%$

Purity: 97.0%

Sample 1-2

Difference between the theoretical value and the actual measured value obtained in the elemental analysis of carbon=−0.56%, $D_{carbon}$=0.56%

Difference between the theoretical value and the actual measured value obtained in the elemental analysis of hydrogen=+0.33%, $D_{hydrogen}$=0.33%

Difference between the theoretical value and the actual measured value obtained in the elemental analysis of nitrogen=+0.13%, $D_{nitrogen}$=0.13%

$D_{max}=D_{carbon}=0.56\%$

Purity: 99.4%

Determination of Purity of Compounds 2 and 3

The purity of the samples of compound 2 (sample 2-1 (Comparative Example 2-1) and sample 2-2 (Example 2-2)) and the samples of compound 3 (sample 3-1 (Comparative Example 3-1) and sample 3-2 (Comparative Example 3-2)) were determined by elemental analysis in the same procedure as that for purity determination for the samples of compound 1. The following shows the results.

Sample 2-1
Difference between the theoretical value and the actual measured value obtained in the elemental analysis of carbon=−3.41%, $D_{carbon}$=3.41%
Difference between the theoretical value and the actual measured value obtained in the elemental analysis of hydrogen=+1.09%, $D_{hydrogen}$=1.09%
Difference between the theoretical value and the actual measured value obtained in the elemental analysis of nitrogen=+0.73%, $D_{nitrogen}$=0.73%

$$D_{max}=D_{carbon}=3.41\%$$

Purity: 96.6%
Sample 2-2
Difference between the theoretical value and the actual measured value obtained in the elemental analysis of carbon=+0.71%, $D_{carbon}$=0.71%
Difference between the theoretical value and the actual measured value obtained in the elemental analysis of hydrogen=+0.29%, $D_{hydrogen}$=0.29%
Difference between the theoretical value and the actual measured value obtained in the elemental analysis of nitrogen=+0.18%, $D_{nitrogen}$=0.18%

$$D_{max}=D_{carbon}=0.71\%$$

Purity: 99.3%
Sample 3-1
Difference between the theoretical value and the actual measured value obtained in the elemental analysis of carbon=−1.18%, $D_{carbon}$=1.18%
Difference between the theoretical value and the actual measured value obtained in the elemental analysis of hydrogen=+0.04%, $D_{hydrogen}$=0.04%
Difference between the theoretical value and the actual measured value obtained in the elemental analysis of nitrogen=+0.06%, $D_{nitrogen}$=0.06%

$$D_{max}=D_{carbon}=1.18\%$$

Purity: 98.8%
Sample 3-2
Difference between the theoretical value and the actual measured value obtained in elemental analysis of carbon=+0.30%, $D_{carbon}$=0.33%
Difference between the theoretical value and the actual measured value obtained in the elemental analysis of hydrogen=+0.20%, $D_{hydrogen}$=0.20%
Difference between the theoretical value and the actual measured value obtained in the elemental analysis of nitrogen=+0.22%, $D_{nitrogen}$=0.22%

$$D_{max}=D_{carbon}=0.33\%$$

Purity: 99.7%

Using each sample, a solar cell was prepared in accordance with the following procedure, and performance evaluation was conducted.

Performance Test Example 1

In accordance with the following procedure, solar cells for testing were prepared using sample 1-1 or sample 1-2 obtained in Production Examples above as an n-type semiconductor material, P3HT (poly-3-hexylthiophene) or PTB7 as a p-type semiconductor material, PEDOT:PSS (poly(3,4-ethylene dioxythiophene):poly(4-styrenesulfonate)) as a charge transport layer material, and ITO (indium tin oxide) (positive electrode) and aluminium (negative electrode) as electrodes. The performance of the cells was evaluated.

(1) Preparation of Solar Cell for Testing

Solar cells for testing were prepared in accordance with the following procedure.

1) Pretreatment on Substrate

An ITO patterning glass plate (manufactured by Sanyo Vacuum Industries Co., Ltd.) was subjected to ultrasonic cleaning with toluene, acetone, water, and IPA (isopropyl alcohol) in this order for 15 minutes for each.

Subsequently, the ITO glass plate was placed in a UV ozone cleaner (Filgen, Inc., UV253), and washed first with oxygen gas for 6 minutes, and then washed with ozone gas for 30 to 60 minutes, followed by washing with nitrogen gas for 2 minutes.

2) Preparation of PEDOT:PSS Thin Film

A PEDOT:PSS thin film was formed as a charge transport layer on the ITO glass plate pretreated in section 1) above using a PEDOT:PSS mixture solution with a ABLE/ASS-301 spin-coating-film-forming apparatus.

The spin coating was carried out at 500 rpm (5 seconds) and 3,000 rpm (1 minute). The formed PEDOT:PSS thin film had a film thickness of about 30 nm.

3) Annealing

The ITO plate having the PEDOT:PSS thin film disposed on its surface obtained in section 2) above was placed on a hot plate and annealed at 135° C. in an air atmosphere for 10 minutes. After annealing, the ITO plate was cooled to room temperature.

4) Preparation of Organic Semiconductor Film

Using a spin-coating-film-forming apparatus (manual spinner, Mikasa Co., Ltd., MS-100), a solution containing pre-dissolved P3HT or PTB7 and sample 1-1 or 1-2 of compound 1 was spin coated on the PEDOT:PSS thin film at 1,200 rpm for 2 minutes, thereby giving a laminate comprising an organic semiconductor thin film (photo conversion layer) having a thickness of about 100 to 150 nm.

The solvent used for the solution was chlorobenzene (diiodooctane was added in an amount of 3% (v/v)).

5) Vacuum Deposition of Metal Electrode

The laminate prepared in section 4) above was placed on a mask in a compact high-vacuum deposition apparatus (Eiko Co., Ltd. VX-20), and a calcium layer of 30 nm and an aluminium layer of 80 nm were deposited thereon in series as a negative electrode using the deposition apparatus.

(2) Current Measurement by Pseudo Solar Light Irradiation

Current measurement using pseudo solar light irradiation was conducted by using SourceMeter (Keithley, Model 2400), current-voltage measuring software and a solar simulator (San-Ei Electric Co., Ltd., XES-3015).

The solar cells for testing prepared in section (1) were irradiated with a given amount of pseudo solar light, and the generated current and voltage were measured. Energy conversion efficiency was then determined by the following equation.

Table 1 shows the measurement results of short-circuit current, open voltage, fill factor (FF), and conversion efficiency. The conversion efficiency is a value determined by the following equation.

$$\text{Conversion efficiency } \eta(\%)=FF(V_{oc} \times J_{sc}/P_{in}) \times 100$$

FF: Fill Factor, $V_{oc}$: Open voltage, $J_{sc}$: Short-circuit Current, $P_{in}$: Intensity of Incident Light (Density)

TABLE 1

| | Sample of Compound 1 | Purity of Compound 1 | p-type Semi-conductor Material | Short-circuit Current (mA/cm$^2$) | Open Voltage (V) | FF | Conversion Efficiency (%) |
|---|---|---|---|---|---|---|---|
| Comparative Example 1-1 | Sample 1-1 | 97.0% | P3HT | 7.07 | 0.49 | 0.37 | 1.26 |
| Example 1-1 | Sample 1-2 | 99.4% | P3HT | 8.31 | 0.59 | 0.49 | 2.41 |
| Carparative Example 1-2 | Sample 1-1 | 97.0% | PTB7 | 9.86 | 0.73 | 0.48 | 3.41 |
| Example 1-2 | Sample 1-2 | 99.4% | PTB7 | 14.22 | 0.74 | 0.62 | 6.59 |

As is clear from Table 1, when compound 1 having a purity of 99.4% was used, the conversion efficiency was significantly higher than when compound 1 having a purity of 97% was used. When PTB7 was used as a p-type semiconductor material in combination with compound 1 as an n-type semiconductor material, the conversion efficiency was significantly higher than when P3HT was used. When compound 1 having a purity of 99.4% and PTB7 were used in combination as an n-type semiconductor material and a p-type semiconductor material, respectively, the conversion efficiency was strikingly higher.

Performance Test Example 2

Solar cells for testing were prepared in the same manner as in Performance Test Example 1 using sample 2-1 or sample 2-2 obtained in Production Example 2 as an n-type semiconductor material. The performance of the cells was evaluated. Table 2 shows the results.

TABLE 2

| | Sample of Compound 2 | Purity of Compound 2 | p-type Semi-conductor Material | Short-circuit Current (mA/cm$^2$) | Open Voltage (V) | FF | Conversion Efficiency (%) |
|---|---|---|---|---|---|---|---|
| Comparative Example 2-1 | Sample 2-1 | 96.6% | P3HT | 5.85 | 0.47 | 0.39 | 1.05 |
| Example 2-1 | Sample 2-2 | 99.3% | P3HT | 8.31 | 0.58 | 0.49 | 2.39 |
| Example 2-2 | Sample 2-2 | 99.3% | PTB7 | 14.21 | 0.76 | 0.67 | 7.27 |

Performance Test Example 3

Solar cells for testing were prepared in the same manner as in Performance Test Example 1 using sample 3-1 or sample 3-2 obtained in Production Example 3 as an n-type semiconductor material. The performance of the cells was evaluated. Table 3 shows the results.

TABLE 3

| | Sample of Compound 3 | Purity of Compound 3 | p-type Semi-conductor Material | Short-circuit Current (mA/cm$^2$) | Open Voltage (V) | FF | Conversion Efficiency (%) |
|---|---|---|---|---|---|---|---|
| Comparative Example 3-1 | Sample 3-1 | 98.8% | P3HT | 8.69 | 0.64 | 0.31 | 1.75 |
| Example 3-1 | Sample 3-2 | 99.7% | P3HT | 7.06 | 0.65 | 0.51 | 2.34 |
| Comparative Example 3-2 | Sample 3-1 | 98.8% | PTB7 | 13.65 | 0.78 | 0.53 | 5.63 |
| Example 3-2 | Sample 3-2 | 99.7% | PTB7 | 14.03 | 0.79 | 0.61 | 6.83 |

The invention claimed is:

1. A process of preparing an n-type semiconductor material consisting of a fullerene derivative having a purity of 99% or more as defined below, wherein the fullerene derivative is represented by formula (1):

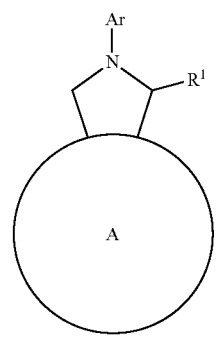

(1)

wherein ring A is a C$_{70}$ fullerene;

R$^1$ is aryl optionally substituted with at least one halogen; and

Ar is aryl optionally substituted with at least one alkyl group, wherein the purity is defined by the following equation:

Purity (%)=100−D$_{max}$ (%)

wherein the $D_{max}$ is the maximum value among the absolute value of the difference between an analysis value and a theoretical value obtained in an elemental analysis of carbon, the absolute value of the difference between an analysis value and a theoretical value obtained in an elemental analysis of hydrogen, and the absolute value of the difference between an analysis value and a theoretical value obtained in an elemental analysis of nitrogen, the process comprising:
(a) modifying a $C_{60}$ fullerene to obtain a fullerene derivative of formula (I),
(b) separating the obtained fullerene derivative of formula (I) with silica gel chromatography using a developing solvent selected from the group consisting of hexane-chloroform, hexane-toluene and hexane-carbon disulfide to obtain a separated fullerene derivative of formula (I),
(c) purifying the separated fullerene derivative of formula (I) with gel permeation chromatography (GPC) using a developing solvent selected from the group consisting of chloroform and toluene to obtain a purified fullerene derivative of formula (I), and
(d) washing and recrystallizing the purified fullerene derivative of formula (I) with an organic solvent to obtain the fullerene derivative having a purity of 99% or more, wherein the washing is conducted with an organic solvent selected from the group consisting of methanol and acetone.

2. A thin-film solar cell comprising the n-type semiconductor material made according to the process of claim 1.

3. An organic power-generating layer comprising the n-type semiconductor material made according to the process of claim 1 and a p-type semiconductor material.

4. The organic power-generating layer according to claim 3, wherein
the p-type semiconductor material consists of a donor-acceptor type π-conjugated polymer,
the donor-acceptor type π-conjugated polymer has a donor unit selected from the group consisting of benzodithiophene, dithienosilole, and N-alkyl carbazole, and
the donor-acceptor type π-conjugated polymer has an acceptor unit selected from the group consisting of benzothiadiazole, thienothiophene, and thiophene pyrrole dione.

5. The organic power-generating layer according to claim 4, wherein the donor-acceptor type π-conjugated polymer is poly(thieno[3,4-b]thiophene-co-benzo[1,2-b:4,5-b']thiophene), or poly(dithieno[1,2-b:4,5-b'][3,2-b:2',3'-d]silole-alt-(2,1,3-benzothiadiazole).

6. The organic power-generating layer according to claim 4, wherein the donor-acceptor type π-conjugated polymer is poly(thieno[3,4-b]thiophene-co-benzo[1,2-b:4,5-b]thiophene).

7. The organic power-generating layer according to claim 3, wherein the p-type semiconductor material is poly-3-hexylthiophene, or poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]].

8. The organic power-generating layer according to claim 3, further comprising diiodooctane.

9. A photoelectric conversion element comprising the organic power-generating layer according to claim 3.

10. The photoelectric conversion element according to claim 9, which is an organic thin-film solar cell.

* * * * *